US006962905B1

(12) United States Patent
Gustafsson

(10) Patent No.: US 6,962,905 B1
(45) Date of Patent: Nov. 8, 2005

(54) PHARMACEUTICAL FORMULATION COMPRISING A LOW MOLECULAR WEIGHT THROMBIN INHIBITOR AND ITS PRODRUG

(75) Inventor: David Gustafsson, Kullavik (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/582,863

(22) PCT Filed: Apr. 19, 2000

(86) PCT No.: PCT/SE00/00756

§ 371 (c)(1),
(2), (4) Date: Jul. 6, 2000

(87) PCT Pub. No.: WO00/64470

PCT Pub. Date: Nov. 2, 2000

(30) Foreign Application Priority Data

Apr. 21, 1999 (SE) .................................. 9901442
Dec. 3, 1999 (SE) .................................. 9904419

(51) Int. Cl.$^7$ ...................... A61K 38/06; A61K 38/55; A61K 49/00
(52) U.S. Cl. .......................... 514/18; 514/20; 514/247; 424/9.1; 544/238; 544/239; 544/240; 560/34; 560/35; 560/168; 560/169; 562/439; 562/560
(58) Field of Search ............................ 514/18, 20, 247, 514/252; 540/593–595, 362; 544/238, 239, 544/240; 546/246; 548/128, 131, 190, 214, 548/233, 535, 566, 326.5; 560/34, 35, 168, 560/169; 562/439, 560, 15; 564/123, 15; 558/170; 424/9.1

(56) References Cited

U.S. PATENT DOCUMENTS

| | | | |
|---|---|---|---|
| 4,346,078 A | 8/1982 | Bajusz et al. | |
| 5,705,487 A | 1/1998 | Schacht et al. | |
| 5,707,966 A | 1/1998 | Schacht et al. | |
| 5,710,130 A | 1/1998 | Schacht et al. | |
| 5,795,892 A | 8/1998 | Von Der Saal et al. | |
| 5,824,679 A | 10/1998 | Von Der Saal et al. | |
| 6,087,380 A | 7/2000 | Hauel et al. | |
| 6,602,871 B2 * | 8/2003 | Lam et al. | .................. 514/249 |

FOREIGN PATENT DOCUMENTS

| | | |
|---|---|---|
| CA | 2156729 | 9/1994 |
| EP | 0 195 212 A2 | 9/1986 |
| EP | 0 293 881 | 12/1988 |
| EP | 0 362 002 A1 | 4/1990 |
| EP | 0 526 877 A2 | 2/1993 |
| EP | 0 526 877 A3 | 2/1993 |
| EP | 0 530 167 A1 | 3/1993 |
| EP | 0 542 525 A2 | 5/1993 |
| EP | 0 601 459 A2 | 6/1994 |
| EP | 0 623 596 A1 | 11/1994 |
| EP | 0 648 780 A1 | 4/1995 |
| EP | 0 669 317 A1 | 8/1995 |
| EP | 0686042 | 12/1995 |
| EP | 0687253 | 12/1998 |
| EP | 0 364 344 | 4/1999 |
| NZ | 262 725 | 5/1997 |
| WO | 94/20467 | 9/1944 |
| WO | 93/05069 | 3/1993 |
| WO | 93/11152 | 6/1993 |
| WO | 93/18060 | 9/1993 |
| WO | 94/29336 | 8/1995 |
| WO | 95/23609 | 8/1995 |
| WO | 95/35309 | 12/1995 |
| WO | 96/03374 | 2/1996 |
| WO | 96/06832 | 3/1996 |
| WO | 96/06849 | 3/1996 |
| WO | 96/16671 | 6/1996 |
| WO | 96/25426 | 8/1996 |
| WO | 96/31504 | 10/1996 |
| WO | 96/32110 | 10/1996 |
| WO | 97/01338 | 1/1997 |
| WO | 97/02284 | 1/1997 |
| WO | 97/11693 | 4/1997 |
| WO | 97/15190 | 5/1997 |
| WO | 97/23499 | 7/1997 |
| WO | 97/24135 | 7/1997 |
| WO | 97/30708 | 8/1997 |
| WO | 97/40024 | 10/1997 |
| WO | 97/46577 | 12/1997 |
| WO | 97/47299 | 12/1997 |
| WO | 97/49404 | 12/1997 |
| WO | 98/01422 | 1/1998 |
| WO | 98/06740 | 2/1998 |
| WO | 98/06741 | 2/1998 |
| WO | 98/37075 | 8/1998 |

(Continued)

OTHER PUBLICATIONS

Claeson, G., "Synthetic peptides and peptidomimeics . . . ," Blood Coagulation and Fibrinolysis, vol. 5, pp. 411-436 (1994).

(Continued)

*Primary Examiner*—Jon Weber
*Assistant Examiner*—Chih-Min Kam
(74) *Attorney, Agent, or Firm*—Nixon & Vanderhye

(57) ABSTRACT

A kit of parts containing (a) a pharmaceutical formulation including a low molecular weight thrombin inhibitor, or a pharmaceutically acceptable derivative thereof, in admixture with a pharmaceutically acceptable adjuvant, diluent or carrier, and (b) a pharmaceutical formulation including a prodrug of a low molecular weight thrombin inhibitor, or a pharmaceutically acceptable derivative of that prodrug, in admixture with a pharmaceutically acceptable adjuvant, diluent or carrier. Components (a) and (b) are each provided in a form that is suitable for administration in conjunction with the other. The kit is useful in the treatment of conditions in which inhibition of thrombin is required or desired.

34 Claims, No Drawings

FOREIGN PATENT DOCUMENTS

| | | |
|---|---|---|
| WO | 98/57932 | 12/1998 |
| WO | 99/00371 | 1/1999 |
| WO | 99/28297 | 6/1999 |
| WO | 99/29664 | 6/1999 |
| WO | 99/29670 | 6/1999 |
| WO | 99/37611 | 7/1999 |
| WO | 99/37668 | 7/1999 |
| WO | 99/40072 | 8/1999 |
| WO | 99/54313 | 10/1999 |
| WO | 00/01704 | 1/2000 |
| WO | 00/08014 | 2/2000 |

OTHER PUBLICATIONS

"Prevention of Venous Thromboembolis," Chest, vol. 114, No. 5, pp. 531S-560S (1998).

Eriksson et al, "Prevention of deep-vein thrombosis after . . . ," Lancet, vol. 347, pp. 635-639 (1996).

Eriksson et al., "Pharmacokinetics and Pharmacodynamics . . . " Thromb Haemost, vol. 81, pp. 358-363 (1999).

Ignasiak et al," Effects of Intravenous Enoxaparin and Intravenous . . . ," Journal of Thrombosis and Thromolysis, vol. 6, pp. 199-200 (1998).

Davidson, Bruce; "1995 American College of Chest Phsyicians (ACCP) Consensus Guidelines on Antithrombotic Therapy"; Seminars in Thrombosis and Hemostasis, 22 Suppl. 2 (1996) 1.

Clagett, G.P., et al; "Prevention of Venous Thromboembolism"; Fourth ACCP Consensus Conference on Antithrombotic Therapy, Chest, 108 (1995) 312S.

* cited by examiner

PHARMACEUTICAL FORMULATION COMPRISING A LOW MOLECULAR WEIGHT THROMBIN INHIBITOR AND ITS PRODRUG

This application is a 371 of PCT/SE00/00756, filed Apr. 19, 2000, which claims priority of Sweden Application No. 9901442-5, filed Apr. 21, 1999, and Sweden Application No. 9904419-0, filed Dec. 3, 1999.

FIELD OF THE INVENTION

This invention relates to a new use of low molecular weight thrombin inhibitors.

BACKGROUND AND PRIOR ART

Blood coagulation is the key process involved in both haemostasis (i.e. the prevention of blood loss from a damaged vessel) and thrombosis (i.e. the formation of a blood clot in a blood vessel, sometimes leading to vessel obstruction).

Coagulation is the result of a complex series of enzymatic reactions. One of the ultimate steps in this series of reactions is the conversion of the proenzyme prothrombin to the active enzyme thrombin.

Thrombin is known to play a central role in coagulation. It activates platelets, leading to platelet aggregation, converts fibrinogen into fibrin monomers, which polymerise spontaneously into fibrin polymers, and activates factor XIII, which in turn crosslinks the polymers to form insoluble fibrin. Furthermore, thrombin activates factor V and factor VIII leading to a "positive feedback" generation of thrombin from prothrombin.

Effective inhibitors of thrombin are thus known, and/or are expected, to be useful as anticoagulants and therefore useful in the therapeutic treatment of thrombosis and related disorders.

The early development of low molecular weight inhibitors of thrombin has been described by Claesson in Blood Coagul. Fibrinol. (1994) 5, 411. Low molecular weight thrombin inhibitors have been described more recently in U.S. Pat. No. 4,346,078; International Patent Applications WO 93/11152, WO 93/18060, WO 93/05069, WO 94/20467, WO 94/29336, WO 95/35309, WO 95/23609, WO 96/03374, WO 96/06832, WO 96/06849, WO 96/25426, WO 96/32110, WO 97/01338, WO 97/02284, WO 97/15190, WO 97/30708, WO 97/40024, WO 97/46577, WO 98/06740, WO 97/49404, WO 97/11693, WO 97/24135, WO 97/47299, WO 98/01422, WO 98/57932, WO 99/29664, WO 98/06741, WO 99/37668, WO 99/37611, WO 98/37075, WO 99/00371, WO 99/28297, WO 99/29670, WO 99/40072, WO 99/54313, WO 96/31504, WO 00/01704 and WO 00/08014; and European Patent Applications 648 780, 468 231, 559 046, 641 779, 185 390, 526 877, 542 525, 195 212, 362 002, 364 344, 530 167, 293 881, 686 642, 669 317, 601 459 and 623 596.

In particular, international patent application WO 94/29336 discloses a group of compounds, including HOOC—$CH_2$—(R)Cgl—Aze—Pab—H (in which Cgl represents cyclohexylglycine, Aze represents S-azetidine-2-carboxylic acid and Pab—H represents 4-aminomethylamidinobenzene), which is also known as melagatran (see Example 1 of WO 94/29336). International Patent Application WO 97/23499 discloses prodrugs of inter alia melagatran.

None of the above-mentioned documents disclose or suggest the administration of an active thrombin inhibitor in conjunction with a prodrug of that thrombin inhibitor, or indeed in conjunction with a prodrug of any thrombin inhibitor.

Deep venous thrombosis (DVT) and pulmonary embolism (PE) are major health problems, which may give rise to serious outcomes. In particular, PE may be fatal, or may result in the development of pulmonary hypertension and heart failure from recurrent embolism. DVT may result in post-thrombotic venous insufficiency and ulcers in the affected part of the body (e.g. leg). Both are common conditions, which have a great impact on worldwide healthcare costs.

There is a considerable incidence of DVT and PE following orthopaedic surgery. For example, in patients undergoing total hip replacement, the incidence of DVT in the absence of thromboprophylaxis may be as high as 45 to 57%. Further, the incidence of proximal DVT may be between 23 and 36%, and that of fatal PE, 0.34 to 6%. In patients undergoing total knee replacement in the absence of thromboprophylaxis, the postoperative incidence of DVT is between 40 and 84%, of proximal DVT is between 9 and 20%, and of fatal PE is between 0.2 and 0.7%. In patients undergoing general surgery in the absence of thromboprophylaxis, the postoperative incidence of DVT is about 25%. (Reference: Chest (1998) 114, 531S to 560S.)

Low-dose, subcutaneous (s.c.) unfractionated heparin is the most widely used current prophylactic treatment for venous thromboembolism resulting from orthopaedic and general surgery. The incidence of DVT after total hip replacement has been shown to be reduced (see Chest reference above).

The use of low-molecular weight heparin (LMWH) in the prophylaxis of DVT following total hip and knee replacement operations has been shown to further the reduce incidence (when compared to low dose unfractionated heparin), without a concomitant increase in bleeding (see Chest reference above).

However, prolonged treatment with heparins has been shown to give rise to an increased risk of osteoporosis. Heparins may also give rise to "heparin-induced thrombocytopenia" (HIT), are dependent on the plasma level of the endogenous thrombin inhibitor, antithrombin, and do not inactivate clot-bound thrombin.

Oral anticoagulants, such as warfarin (a vitamin K antagonist), has also been shown to be effective in reducing DVT after major surgery (see Chest reference above). However, due to the risk of bleeding, and the need for frequent laboratory control, the use of this substance is generally reserved for high risk patients, and/or for long term use. Vitamin K antagonists also demonstrate a notable risk of interaction with other drugs and certain foods, and their use requires monitoring of the patient's blood coagulation status.

Antiplatelet agents, such as aspirin, have been shown to have limited efficacy in preventing DVT (see Chest reference above).

Comparative clinical studies carried out during the course of total hip replacement operations have shown that subcutaneous administration of the thrombin inhibitor hirudin is superior to unfractionated heparin and LMWH in reducing the frequency of total and proximal DVT with no corresponding increase in bleeding (see Eriksson et al in Lancet, 347, 635 (1996) and J. Bone Joint. Surg., Sep., 11 (1996)). However, hirudin is expensive and has an immunogenic potential.

Thus, there is a need for effective treatments of thrombotic conditions such as DVT.

DISCLOSURE OF THE INVENTION

We have found, surprisingly, that administration of a low molecular weight thrombin inhibitor in conjunction with a prodrug of a (or a prodrug of that) thrombin inhibitor gives rise to a notable anticoagulant effect.

According to a first aspect of the invention there is provided a kit of parts comprising components:
(a) a pharmaceutical formulation including a low molecular weight thrombin inhibitor, or a pharmaceutically acceptable derivative thereof, in admixture with a pharmaceutically acceptable adjuvant, diluent or carrier; and
(b) a pharmaceutical formulation including a prodrug of a low molecular weight thrombin inhibitor, or a pharmaceutically acceptable derivative of that prodrug, in admixture with a pharmaceutically acceptable adjuvant, diluent or carrier, which components (a) and (b) are each provided in a form that is suitable for administration in conjunction with the other.

It is preferred that the prodrug of component (b) is a prodrug of the active low molecular weight thrombin inhibitor of component (a).

According to a further aspect of the invention, there is provided a method of making a kit of parts as defined herein, which method comprises bringing a component (a), as defined above, into association with a component (b), as defined above, thus rendering the two components suitable for administration in conjunction with each other.

By bringing the two components "into association with" each other, we include that components (a) and (b) may be:
(i) provided as separate formulations (i.e. independently of one another), which are subsequently brought together for use in conjunction with each other in combination therapy; or
(ii) packaged and presented together as separate components of a "combination pack" for use in conjunction with each other in combination therapy.

Thus, there is further provided a kit of parts comprising:
(1) one of components (a) and (b) as defined herein; together with
(2) instructions to use that component in conjunction with the other of the two components.

The kits of parts defined herein may comprise more than one formulation including an appropriate quantity/dose of thrombin inhibitor, and/or more than one formulation including an appropriate quantity/dose of respective prodrug, in order to provide for repeat dosing. If more than one formulation (comprising thrombin inhibitor or prodrug) is present, such formulations may be the same, or may be different in terms of the dose of thrombin inhibitor/prodrug, chemical composition and/or physical form.

A further aspect of the invention provides a method of treatment of a condition in which inhibition of thrombin is required or desired, which comprises administration of:
(a) a pharmaceutical formulation including a low molecular weight thrombin inhibitor, or a pharmaceutically acceptable derivative thereof, in admixture with a pharmaceutically acceptable adjuvant, diluent or carrier; in conjunction with
(b) a pharmaceutical formulation including a prodrug of a low molecular weight thrombin inhibitor, or a pharmaceutically acceptable derivative of that prodrug, in admixture with a pharmaceutically acceptable adjuvant, diluent or carrier, to a patient suffering from, or susceptible to, such a condition.

For the avoidance of doubt, as used herein, the term "trearment" includes therapeutic and/or prophylactic treatment.

"Pharmaceutically acceptable derivatives" of thrombin inhibitors and prodrugs includes salts (e.g. pharmaceutically acceptable non-toxic organic or inorganic acid addition salts) and solvates. It will be appreciated that the term pharmaceutically acceptable derivatives of active thrombin inhibitors includes those derivatives that have the same biological function and/or activity as that thrombin inhibitor but, for the purposes of this invention, does not include prodrugs of that thrombin inhibitor.

By "administration in conjunction with", we include that respective formulations comprising thrombin inhibitor and/or prodrug are administered, sequentially, separately and/or simultaneously, over the course of treatment of the relevant condition, which condition may be acute or chronic. Preferably, the term includes that the two formulations are administered (optionally repeatedly) sufficiently closely in time for there to be a beneficial effect for the patient, that is greater, over the course of the treatment of the relevant condition, than if either of the two formulations are administered (optionally repeatedly) alone, in the absence of the other formulation, over the same course of treatment. Determination of whether a combination provides a greater beneficial effect in respect of, and over the course of treatment of, a particular condition, will depend upon the condition to be treated or prevented, but may be achieved routinely by the skilled person.

Thus, the term "in conjunction with" includes that one or other of the two formulations may be administered (optionally repeatedly) prior to, after, and/or at the same time as, administration with the other component. When used in this context, the terms "administered simultaneously" and "administered at the same time as" include that individual doses of thrombin inhibitor and prodrug are administered within 48 hours (e.g. 24 hours) of each other.

Components (a) and (b) as described herein may also be presented (i.e. formulated) as a combined preparation (i.e. presented as a single formulation including low molecular thrombin inhibitor and prodrug).

Thus, there is further provided a pharmaceutical formulation including a low molecular weight thrombin inhibitor (or a pharmaceutically acceptable derivative thereof) and a prodrug of a low molecular weight thrombin inhibitor (or a pharmaceutically acceptable derivative of that prodrug), in admixture with a pharmaceutically acceptable adjuvant, diluent or carrier.

The term "low molecular weight thrombin inhibitor" will be understood by those skilled in the art. The term may also be understood to include any composition of matter (e.g. chemical compound) which inhibits thrombin to an experimentally determinable degree in in vivo and/or in in vitro tests, and which possesses a molecular weight of below 2,000, preferably below 1,000.

Preferred low molecular weight thrombin inhibitors include low molecular weight peptide-based, amino acid-based, and/or peptide analogue-based, thrombin inhibitors.

The term "low molecular weight peptide-based, amino acid-based, and/or peptide analogue-based, thrombin inhibitors" will be well understood by one skilled in the art to include low molecular weight thrombin inhibitors with one to four peptide linkages, and includes those described in the review paper by Claesson in Blood Coagul. Fibrin. (1994) 5, 411, as well as those disclosed in U.S. Pat. No. 4,346,078; International Patent Applications WO 93/11152, WO 93/18060, WO 93/05069, WO 94/20467, WO 94/29336, WO 95/35309, WO 95/23609, WO 96/03374, WO 96/06832, WO 96/06849, WO 96/25426, WO 96/32110, WO 97/01338, WO 97/02284, WO 97/15190, WO 97/30708, WO 97/40024, WO 97/46577, WO 98/06740, WO 97/49404, WO 97/11693, WO 97/24135, WO 97/47299, WO 98/01422, WO 98/57932, WO 99/29664, WO 98/06741, WO 99/37668, WO 99/37611, WO 98/37075, WO 99/00371, WO 99/28297, WO 99/29670, WO 99/40072, WO 99/54313, WO 96/31504, WO 00/01704 and WO 00/08014; and European Patent Applications 648 780, 468 231, 559 046, 641 779, 185 390, 526 877, 542 525, 195 212, 362 002, 364 344, 530 167, 293 881, 686 642, 669 317, 601 459 and 623 596, the disclosures in all of which documents are hereby incorporated by reference.

Preferred low molecular weight peptide-based thrombin inhibitors include HOOC—$CH_2$—(R)Cha—Pic—Nag—H (wherein Cha represents cyclohexylalanine, Pic represents (S)-pipecolinic acid and Nag represents noragmatine; known as inogatran; see International Patent Application WO 93/11152) and, especially, HOOC—$CH_2$—(R)Cgl—Aze—Pab—H (known as melagatran; see above and International Patent Application WO 94/29336).

The term "prodrug" of a low molecular weight thrombin inhibitor includes any compound that, following oral or parenteral administration, is metabolised in vivo to form a low molecular weight thrombin inhibitor (as defined herein), in an experimentally-detectable amount, and within a pre-determined time (e.g. within a dosing interval of between 6 and 24 hours (i.e. once to four times daily)), following oral or parenteral administration. Prodrugs of the thrombin inhibitor melagatran that may be mentioned include those disclosed in international patent application WO 97/23499. Preferred prodrugs are those of the formula $R^1O_2C$—$CH_2$—(R)Cgl—Aze—Pab—OH (see the list of abbreviations above or in WO 97/23499), wherein $R^1$ represents $C_{1-10}$ alkyl or benzyl, such as linear or branched $C_{1-6}$ alkyl (e.g. $C_{1-4}$ alkyl, especially methyl, propyl and, particularly, ethyl) and the OH group replaces one of the amidino hydrogens in Pab.

The term "condition in which inhibition of thrombin is required or desired" will be understood by those skilled in the art to include the following:

The treatment and/or prophylaxis of thrombosis and hypercoagulability in blood and tissues of animals including man. It is known that hypercoagulability may lead to thrombo-embolic diseases. Conditions associated with hypercoagulability and thrombo-embolic diseases which may be mentioned include inherited or acquired activated protein C resistance, such as the factor V-mutation (factor V Leiden), and inherited or acquired deficiencies in antithrombin III, protein C, protein S, heparin cofactor II. Other conditions known to be associated with hypercoagulability and thrombo-embolic disease include circulating antiphospholipid antibodies (Lupus anticoagulant), homocysteinemi, heparin induced thrombocytopenia and defects in fibrinolysis.

The treatment of conditions where there is an undesirable excess of thrombin without signs of hypercoagulability, for example in neurodegenerative diseases such as Alzheimer's disease.

Particular disease states which may be mentioned include the therapeutic and/or prophylactic treatment of venous thrombosis (e.g. DVT) and pulmonary embolism, arterial thrombosis (e.g. in myocardial infarction, unstable angina, thrombosis-based stroke and peripheral arterial thrombosis) and systemic embolism usually from the atrium during arterial fibrillation or from the left ventricle after transmural myocardial infarction, or caused by congestive heart failure; prophylaxis of re-occlusion (ie thrombosis) after thrombolysis, percutaneous trans-luminal angioplasty (PTA) and coronary bypass operations; the prevention of re-thrombosis after microsurgery and vascular surgery in general.

Further indications include the therapeutic and/or prophylactic treatment of disseminated intravascular coagulation caused by bacteria, multiple trauma, intoxication or any other mechanism; anticoagulant treatment when blood is in contact with foreign surfaces in the body such as vascular grafts, vascular stents, vascular catheters, mechanical and biological prosthetic valves or any other medical device; and anticoagulant treatment when blood is in contact with medical devices outside the body such as during cardiovascular surgery using a heart-lung machine or in haemodialysis; the therapeutic and/or prophylactic treatment of idiopathic and adult respiratory distress syndrome, pulmonary fibrosis following treatment with radiation or chemotherapy, septic shock, septicemia, inflammatory responses, which include, but are not limited to, edema, acute or chronic atherosclerosis such as coronary arterial disease, cerebral arterial disease, peripheral arterial disease, reperfusion damage, and restenosis after percutaneous trans-luminal angioplasty (PTA).

Preferred conditions include thrombosis, especially DVT, including distal and proximal DVT. The present invention finds particular utility in the prophylactic treatment of DVT resulting from surgery, such as gastrointestinal, or orthopaedic, surgery (e.g. hip or knee replacement). This includes DVT resulting from immobilisation after surgery.

In accordance with the invention, thrombin inhibitors, prodrugs of thrombin inhibitors, and derivatives of either, may be administered orally, intravenously, subcutaneously, buccally, rectally, dermally, nasally, tracheally, bronchially, topically, by any other parenteral route, or via inhalation, in the form of a pharmaceutical preparation comprising the thrombin inhibitor or prodrug in a pharmaceutically acceptable dosage form. Depending on the disorder, and the patient, to be treated, as well as the route of administration, the compositions may be administered at varying doses.

Preferred modes of delivery are systemic. For melagatran and derivatives thereof, preferred modes of administration are parenteral, more preferably intravenous, and especially subcutaneous. For prodrugs of melagatran, preferred modes of administration are oral.

In the therapeutic treatment of mammals, and especially humans, thrombin inhibitors, prodrugs of thrombin inhibitors, and derivatives of either will generally be administered as a pharmaceutical formulation in admixture with a pharmaceutically acceptable adjuvant, diluent or carrier, which may be selected with due regard to the intended route of administration and standard pharmaceutical practice.

Suitable formulations for use in administering thrombin inhibitors are known in the art, and include those known from U.S. Pat. No. 4,346,078; International Patent Applications WO 93/11152, WO 93/18060, WO 93/05069, WO 94/20467, WO 94/29336, WO 95/35309, WO 95/23609, WO 96/03374, WO 96/06832, WO 96/06849, WO 96/25426, WO 96/32110, WO 97/01338, WO 97/02284, WO 97/15190, WO 97/30708, WO 97/40024, WO 97/46577, WO 98/06740, WO 97/49404, WO 97/11693, WO 97/24135, WO 97/47299, WO 98/01422, WO 98/57932, WO 99/29664, WO 98/06741, WO 99/37668, WO 99/37611, WO 98/37075, WO 99/00371, WO 99/28297, WO 99/29670, WO 99/40072, WO 99/54313, WO 96/31504, WO 00/01704 and WO 00/08014; and European Patent Applications 648 780, 468 231, 559 046, 641 779, 185 390, 526 877, 542 525, 195 212, 362 002, 364 344, 530 167, 293 881, 686 642, 669 317, 601 459 and 623 596, the disclosures in all of which documents are hereby incorporated by reference.

Suitable formulations for use with melagatran, derivatives and prodrugs thereof are described in the literature, for example as described in inter alia international patent applications WO 94/29336, WO 96/14084, WO 96/16671, WO 97/23499, WO 97/39770, WO 97/45138, WO 98/16252, WO 99/27912 and WO 99/27913, the disclosures in which documents are hereby incorporated by reference. Otherwise, the preparation of suitable formulations may be achieved non-inventively by the skilled person using routine techniques.

The amounts of thrombin inhibitor, prodrug, or derivative of either, in the formulation will depend on the severity of the condition, and on the patient, to be treated, as well as the compound(s) which is/are employed, but may be determined non-inventively by the skilled person.

Suitable doses of thrombin inhibitors, prodrugs and derivatives of either, in the therapeutic and/or prophylactic treatment of mammalian, especially human, patients may be determined routinely by the medical practitioner or other skilled person, and include the respective doses discussed in the prior art documents disclosing thrombin inhibitors that are mentioned hereinbefore, the disclosures in which are hereby incorporated by reference.

In the case of melagatran, suitable doses of active compound, prodrugs and derivatives thereof, in the therapeutic and/or prophylactic treatment of mammalian, especially human, patients include those which give a mean plasma concentration of up to 5 $\mu$mol/L, for example in the range 0.001 to 5 $\mu$mol/L over the course of treatment of the relevant condition. Suitable doses may thus be in the range 0.1 mg once daily to 25 mg three times daily, and/or up to 100 mg infused parenterally over a 24 hour period, for melagatran, and in the range 0.1 mg once daily to 100 mg three times daily for prodrugs of melagatran including those specifically mentioned hereinbefore.

In any event, the physician, or the skilled person, will be able to determine the actual dosage which will be most suitable for an individual patient, which is likely to vary with the condition that is to be treated, as well as the age, weight, sex and response of the particular patient to be treated. The above-mentioned dosages are exemplary of the average case; there can, of course, be individual instances where higher or lower dosage ranges are merited, and such are within the scope of this invention.

The sequence in which the formulations comprising thrombin inhibitor, and prodrug, may be administered (i.e. whether, and at what point, sequential, separate and/or simultaneous administration takes place) may be determined by the physician or skilled person. For example, the sequence may depend upon many factors that will be evident to the skilled person, such as whether, at any time during the course or period of treatment, one or other of the formulations cannot be administered to the patient for practical reasons (e.g. the patient is unconscious and thus unable to take an oral formulation comprising either thrombin inhibitor or prodrug).

For example, in the treatment of thrombosis (e.g. DVT) resulting from surgery, such as gastrointestinal, or orthopaedic, surgery, and when the active thrombin inhibitor is melagatran, it is preferred that the formulation comprising melagatran is administered parenterally within two days (e.g. within 24 hours) of surgery (either prior to or after surgery), and particularly immediately prior to (e.g. within 2 hours), and/or within up to 12 hours after, surgery (e.g. at least one hour after surgery), and thereafter for up to between 3 and 7 (e.g. between 0 and 2, such as between 1 and 2) days after that surgery, and that the formulation comprising prodrug is administered orally within 7 days following that surgery (preferably once administration of melagatran has been terminated) for up to e.g. between 11 and 40 days, preferably 9 days, more preferably up to 8 days.

The method described herein may have the advantage that, in the treatment of conditions in which inhibition of thrombin is required or desired, it may be more convenient for the physician and/or patient than, be more efficacious than, be less toxic than, have a broader range of activity than, be more potent than, produce fewer side effects than, or that it may have other useful pharmacological properties over, similar methods known in the prior art for the treatment of such conditions.

The invention is illustrated, but in no way limited, by the following example.

EXAMPLE 1

Clinical Trial—Melagatran and EtOOC—CH$_2$—(R) Cgl—Aze—Pab—OH Combination Therapy A controlled, randomised, parallel group, Swedish multi-centre pilot study was carried out. The study was open with regard to the drugs under evaluation but was blind for the patients, all personnel at the study sites, and for the person monitoring the experiments with regard to the doses of melagatran and the prodrug of melagatran, EtOOC—CH$_2$—(R)Cgl—Aze—Pab—OH (P; see WO 97/23499).

Dalteparin (Fragmin®; Pharmacia-Upjohn) was used as a reference compound.

Patients scheduled for primary elective total hip or knee replacement were eligible for inclusion, and were randomly selected into one of three groups, each to receive different doses of melagatran and P, or dalteparin. In all, 135 patients were included in the study, of which 105 patients could be used for evaluation with respect to thromboembolic events using central assessment of locally performed phlebograms.

About 32 patients in each treatment group were evaluated according to the protocol. A stratified randomisation, by centre and type of surgery, was used to ensure that approximately equal numbers of patients were given each of the drugs under evaluation at all participating centres (in all six centres were used) for both types of surgery (hip or knee). Each centre received study drugs in blocks of four, separately for hips and knees. Within each block, the order of the study drugs was randomised.

The following formulations were used in the study:
Melagatran—5, 10 or 20 mg/mL in aqueous saline solution.
P—appropriate weight (see below) in a tablet also comprising 59 to 63 mg corn starch, 115 mg microcrystalline cellulose and 2 mg sodium stearyl fumarate.

The following doses of melagatran and P were used in the study:
Treatment A—s.c. melagatran (1 mg) b.i.d. for 2 days, followed by oral administration of P (6 mg) b.i.d. for 6 to 9 days.

Treatment B—s.c. melagatran (2 mg) b.i.d. for 2 days, followed by an oral administration of P (12 mg) b.i.d. for 6 to 9 days.

Treatment C—s.c. melagatran (4 mg) b.i.d. for 2 days, followed by an oral administration of P (24 mg) b.i.d. for 6 to 9 days.

The patients receiving melagatran and P received treatment on the day of surgery. The patient received the first injection after induction of anaesthesia immediately before surgery. For knee-patients, the pre-operative melagatran injection was given before tourniquets were applied. The second injection was given in the evening the same day. The patient received one melagatran injection in the morning and one in the evening over the next 24 hours, until oral administration of P, twice daily, started. The first oral dose of P was always taken in the morning. Thus, the total treatment period was between 8 and 11 days.

Treatment D—dalteparin (Fragmin®): one s.c. injection of 5000 U during the evening of the day before surgery, continuing with one s.c. injection every evening over a treatment period of 8 to 11 days.

The plasma concentrations of melagatran were recorded.

The results of the trial, in terms of the frequencies of thromboembolism after hip or knee surgery, are tabulated below:

|  | Treatment A | | Treatment B | | Treatment C | | Treatment D | |
| --- | --- | --- | --- | --- | --- | --- | --- | --- |
|  | (n) | (%) | (n) | (%) | (n) | (%) | (n) | (%) |
| Outcome | 6/29 | 21 | 6/24 | 25 | 4/24 | 16 | 5/27 | 19 |

These data show that a combination of subcutaneously administered melagatran and orally administered P is effective in preventing DVT after orthopaedic surgery.

What is claimed is:

1. A kit of parts comprising:
   (a) a pharmaceutical formulation comprising a low molecular weight thrombin inhibitor, or a pharmaceutically acceptable salt or solvate thereof, in admixture with a pharmaceutically acceptable adjuvant, diluent or carrier; and
   (b) a pharmaceutical formulation comprising a prodrug of the low molecular weight thrombin inhibitor of formulation (a), or a pharmaceutically acceptable salt or solvate of that prodrug, in admixture with a pharmaceutically acceptable adjuvant, diluent or carrier,
   which formulations (a) and (b) are each provided in a form that is suitable for administration in conjunction with the other.

2. The kit of parts as claimed in claim 1, wherein formulations (a) and (b) are suitable for sequential or simultaneous use in the treatment of a condition in which inhibition of thrombin is required or desired.

3. The kit of parts as claimed in claim 2, wherein the condition is deep venous thrombosis.

4. The kit of parts as claimed in claim 1, wherein the thrombin inhibitor is melagatran.

5. The kit of parts as claimed in claim 4, wherein the prodrug is of the formula

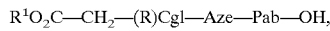

$R^1O_2C$—$CH_2$—(R)Cgl—Aze—Pab—OH, wherein $R^1$ represents linear or branched $C_{1-6}$ alkyl and the OH group replaces one of the amidino hydrogens in Pab.

6. The kit of parts as claimed in claim 5, wherein $R^1$ represents methyl, ethyl or propyl.

7. The kit of parts as claimed in claim 5, wherein $R^1$ represents ethyl.

8. The kit of parts as claimed in claim 1, 4 or 7, wherein the formulation comprising thrombin inhibitor, or salt or solvate thereof is a parenteral formulation and that comprising the prodrug, or salt or solvate of said prodrug, is an oral formulation.

9. The kit of parts comprising:
   (1) one of formulations (a) and (b) as defined in claim 1, 4 or 7; together with
   (2) instructions to use said one formulation in conjunction with the other of the two formulations (a) and (b).

10. A method of making the kit of parts as defined in claim 1, 4 or 7, which method comprises bringing a formulation (a) into association with a formulation (b), thus rendering the two formulations suitable for administration in conjunction with each other.

11. A pharmaceutical formulation comprising:
   (i) a low molecular weight thrombin inhibitor or a pharmaceutically acceptable salt or solvate thereof; and
   (ii) a prodrug of the low molecular weight thrombin inhibitor of component (i) or a pharmaceutically acceptable salt or solvate of that prodrug, in admixture with
   (iii) a pharmaceutically acceptable adjuvant, diluent or carrier.

12. The pharmaceutical formulation as claimed in claim 11 wherein the thrombin inhibitor is melagatran.

13. The pharmaceutical formulation as claimed in claim 12 wherein the prodrug is of the formula

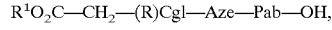

$R^1O_2C$—$CH_2$—(R)Cgl—Aze—Pab—OH, wherein $R^1$ represents linear or branched $C_{1-6}$ alkyl and the OH group replaces one of the amidino hydrogens in Pab.

14. The pharmaceutical formulation as claimed in claim 13 wherein $R^1$ represents methyl, ethyl, or propyl.

15. The pharmaceutical formulation as claimed in claim 13 wherein $R^1$ represents ethyl.

16. A method of treatment of a condition in which inhibition of thrombin is required or desired, which comprises administration of a formulation as defined in claim 11 to a patient suffering from, or susceptible to, such a condition in an effective amount and for a time and under conditions suitable for reducing the incidence of said condition.

17. The method as claimed in claim 16 wherein the condition is deep venous thrombosis.

18. The method as claimed in claim 17 wherein the thrombosis results from surgery.

19. The method as claimed in claim 18 wherein the surgery is gastrointestinal surgery or orthopedic surgery.

20. The method as claimed in claim 16 wherein the thrombin inhibitor is melagatran.

21. The method according to claim 16 wherein the thrombin inhibitor is melagatran, and the prodrug is of formula

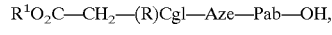

$R^1O_2C$—$CH_2$—(R)Cgl—Aze—Pab—OH, wherein $R^1$ represents linear or branched $C_{1-6}$ alkyl and the OH group replaces one of the amdino hydrogens in Pab.

22. The method as claimed in claim 21, wherein $R^1$ represents methyl, ethyl or propyl.

23. The method as claimed in claim 21, wherein $R^1$ represents ethyl.

24. A method of treatment of a condition in which inhibition of thrombin is required or desired, which comprises administration of
   (a) a pharmaceutical formulation comprising a low molecular weight thrombin inhibitor, or a pharmaceutically acceptable salt or solvate thereof, in admixture with a pharmaceutically acceptable adjuvant, diluent or carrier, in conjunction with (b) a pharmaceutical formulation comprising a prodrug of the low molecular weight thrombin inhibitor of formulation (a), or a pharmaceutically acceptable salt or solvate of that prodrug, in admixture with a pharmaceutically acceptable adjuvant, diluent or carrier, to a patient suffering from, or susceptible to, such a condition in an effective amount and for a time and under conditions suitable for reducing the incidence of said condition.

25. The method as claimed in claim 24 in which the formulation (a) is administered prior to commencement of administration of formulation (b).

26. The method as claimed in claim 24, wherein the condition is deep venous thrombosis.

27. The method as claimed in claim 26, wherein the thrombosis results from surgery.

28. The method as claimed in claim 27, wherein the surgery is gastrointestinal surgery or orthopedic surgery.

29. The method as claimed in claim 27, wherein formulation (a) is administered parenterally prior to or after surgery and formulation (b) is administered orally following that surgery.

30. The method as claimed in claim 27, wherein formulation (a) is administered parenterally prior to and after surgery and formulation (b) is administered orally following that surgery.

31. The method as claimed in claim 24, 26, 27, 28, 29 or 30, wherein the thrombin inhibitor is melagatran.

32. A method of treatment of a condition in which inhibition of thrombin is required or desired, which comprises administration of (a) a pharmaceutical formulation comprising melagatran, or a pharmaceutically acceptable salt or solvate thereof, in admixture with a pharmaceutically acceptable adjuvant, diluent or carrier, in conjunction with (b) a pharmaceutical formulation comprising a prodrug of formula $R^1O_2C-CH_2-(R)Cgl-Aze-Pab-OH$, wherein $R^1$ represents linear or branched $C_{1-6}$ alkyl and the OH group replaces one of the amidino hydrogens in Pab, or a pharmaceutically acceptable salt or solvate of that prodrug, in admixture with a pharmaceutically acceptable adjuvant, diluent or carrier, to a patient suffering from, or susceptible to, such a condition in an effective amount and for a time and under conditions suitable for reducing the incidence of said condition.

33. The method as claimed in claim 32, wherein $R^1$ represents methyl, ethyl or propyl.

34. The method as claimed in claim 32, wherein $R^1$ represents ethyl.

* * * * *